(12) United States Patent
Woodard et al.

(10) Patent No.: US 8,298,187 B2
(45) Date of Patent: Oct. 30, 2012

(54) FLUID INJECTION DEVICE

(75) Inventors: Bryan Woodard, Bloomington, IN (US); James D. Purdy, Lafayette, IN (US); David R. Wagner, West Lafayette, IN (US); Richard B. Sisken, West Lafayette, IN (US); Steven J. Charlebois, West Lafayette, IN (US); Gregory A. Frankland, Unionville, IN (US); Scott K. Philhower, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 414 days.

(21) Appl. No.: 12/498,867

(22) Filed: Jul. 7, 2009

(65) Prior Publication Data

US 2011/0009848 A1    Jan. 13, 2011

(51) Int. Cl.
    *A61M 5/178* (2006.01)
(52) U.S. Cl. ............... 604/164.12; 604/164.01; 604/173
(58) Field of Classification Search .................. 604/158, 604/164.01–164.12, 165.02, 173, 264, 272, 604/509–511, 514–517
    See application file for complete search history.

(56) References Cited

U.S. PATENT DOCUMENTS

| | | | |
|---|---|---|---|
| 2,137,710 A | 11/1938 | Anderson | |
| 3,782,381 A | 1/1974 | Winnie | |
| 4,013,080 A | 3/1977 | Froning | |
| 4,136,695 A | 1/1979 | Dafoe | |
| 4,235,234 A | 11/1980 | Whitney et al. | |
| 4,349,023 A | 9/1982 | Gross | |
| 4,511,356 A | 4/1985 | Froning et al. | |
| 4,578,061 A | 3/1986 | Lemelson | |
| 4,684,369 A | 8/1987 | Wildemeersch | |
| 4,710,176 A | 12/1987 | Quick | |
| 4,759,746 A | 7/1988 | Straus | |
| 4,841,977 A | 6/1989 | Griffith et al. | |
| 4,846,799 A | 7/1989 | Tanaka et al. | |
| 4,872,456 A | 10/1989 | Hasson | |

(Continued)

FOREIGN PATENT DOCUMENTS

JP       2002-306606 A       10/2002

(Continued)

OTHER PUBLICATIONS

Gupta, Sanjay et al., "Technical Innovation: Using a Coaxial Technique with a Curved Inner Needle for CT-Guided Fine-Needle Aspiration Biopsy", AJR, Jul. 2002, vol. 170, pp. 109-112.

(Continued)

*Primary Examiner* — Kevin C. Sirmons
*Assistant Examiner* — Kami A Bosworth
(74) *Attorney, Agent, or Firm* — Brinks Hofer Gilson & Lione

(57) ABSTRACT

A medical device is provided. The device includes a cannula with a lumen and a plurality of apertures and a visually perceptible indicator that is configured to allow the cannula to be positioned at an appropriate rotational position within the patient. A plurality of injection needles are disposed within the lumen and a first handle is fixed with respect to the cannula and a second handle is disposed in conjunction with the first handle and fixed to the proximal portion of each of the plurality of needles, the first handle is translatable with respect to the second handle to translate the plurality of needles from a first position where the distal portions of each of the plurality of needles are disposed within the lumen of the cannula, and a second position where the distal portion of each of the plurality of needles extends out of the lumen through their respective aperture.

15 Claims, 7 Drawing Sheets

U.S. PATENT DOCUMENTS

| | | |
|---|---|---|
| 5,026,350 A | 6/1991 | Tanaka et al. |
| 5,100,383 A | 3/1992 | Lichtenstein |
| 5,116,615 A | 5/1992 | Gokcen et al. |
| 5,152,749 A | 10/1992 | Giesy et al. |
| 5,304,141 A | 4/1994 | Johnson et al. |
| 5,308,358 A | 5/1994 | Bond et al. |
| 5,318,040 A | 6/1994 | Kensey et al. |
| 5,354,279 A | 10/1994 | Höfling |
| 5,360,416 A | 11/1994 | Ausherman et al. |
| 5,419,777 A | 5/1995 | Hofling |
| 5,423,770 A | 6/1995 | Yoon |
| 5,464,395 A | 11/1995 | Faxon et al. |
| 5,507,796 A | 4/1996 | Hasson |
| 5,556,376 A | 9/1996 | Yoon |
| 5,571,083 A | 11/1996 | Lemelson |
| 5,628,734 A | 5/1997 | Hatfalvi |
| 5,672,174 A | 9/1997 | Gough et al. |
| 5,683,384 A | 11/1997 | Gough et al. |
| 5,728,143 A | 3/1998 | Gough et al. |
| 5,810,804 A | 9/1998 | Gough et al. |
| 5,827,276 A | 10/1998 | LeVeen et al. |
| 5,855,576 A | 1/1999 | LeVeen et al. |
| 5,863,290 A | 1/1999 | Gough et al. |
| 5,893,839 A | 4/1999 | Johnson |
| 5,899,909 A | 5/1999 | Claren et al. |
| 5,964,740 A | 10/1999 | Ouchi |
| 5,989,266 A | 11/1999 | Foster |
| 6,009,877 A | 1/2000 | Edwards |
| 6,024,726 A | 2/2000 | Hill |
| 6,056,744 A | 5/2000 | Edwards |
| 6,059,780 A | 5/2000 | Gough et al. |
| 6,071,230 A | 6/2000 | Henalla |
| 6,080,150 A | 6/2000 | Gough |
| 6,129,726 A | 10/2000 | Edwards et al. |
| 6,200,302 B1 | 3/2001 | Johnson |
| 6,203,533 B1 | 3/2001 | Ouchi |
| 6,210,377 B1 | 4/2001 | Ouchi |
| 6,210,378 B1 | 4/2001 | Ouchi |
| 6,217,554 B1 | 4/2001 | Green |
| 6,231,591 B1 | 5/2001 | Desai |
| 6,273,852 B1 | 8/2001 | Lehe et al. |
| 6,302,870 B1 | 10/2001 | Jacobsen et al. |
| 6,319,230 B1 | 11/2001 | Palasis et al. |
| 6,425,887 B1 | 7/2002 | McGuckin et al. |
| 6,432,092 B2 | 8/2002 | Miller |
| 6,454,765 B1 | 9/2002 | Leveen et al. |
| 6,461,296 B1 | 10/2002 | Desai |
| 6,468,273 B1 | 10/2002 | Leveen et al. |
| 6,478,727 B2 | 11/2002 | Seetbon |
| 6,491,703 B1 | 12/2002 | Ulmsten |
| 6,494,887 B1 | 12/2002 | Kaladelfos |
| 6,520,927 B1 | 2/2003 | Unsworth |
| 6,544,230 B1 | 4/2003 | Flaherty et al. |
| 6,572,593 B1 | 6/2003 | Daum |
| 6,575,967 B1 | 6/2003 | Leveen et al. |
| 6,592,559 B1 | 7/2003 | Pakter et al. |
| 6,595,958 B1 | 7/2003 | Mickley |
| 6,616,626 B2 | 9/2003 | Crank et al. |
| 6,638,210 B2 | 10/2003 | Berger |
| 6,685,648 B2 | 2/2004 | Flaherty et al. |
| 6,695,855 B1 | 2/2004 | Gaston |
| 6,702,744 B2 | 3/2004 | Mandrusov et al. |
| 6,706,017 B1 | 3/2004 | Dulguerov |
| 6,730,061 B1 | 5/2004 | Cuschieri et al. |
| 6,802,807 B2 | 10/2004 | Anderson et al. |
| 6,875,219 B2 | 4/2005 | Arramon et al. |
| 6,905,480 B2 | 6/2005 | McGuckin, Jr. et al. |
| 6,911,003 B2 | 6/2005 | Anderson et al. |
| 6,932,759 B2 | 8/2005 | Kammerer et al. |
| 6,939,322 B2 | 9/2005 | Crank et al. |
| 6,989,004 B2 | 1/2006 | Hinchliffe et al. |
| 6,994,693 B2 | 2/2006 | Tal |
| 7,014,607 B2 | 3/2006 | Gellman |
| 7,087,040 B2 | 8/2006 | McGuckin, Jr. et al. |
| 7,106,574 B2 | 9/2006 | Beyerlein |
| 7,120,487 B2 | 10/2006 | Nelson |
| 7,172,576 B2 | 2/2007 | Sawa et al. |
| 7,282,020 B2 | 10/2007 | Kaplan |
| 2001/0037086 A1 | 11/2001 | Gambale et al. |
| 2002/0082546 A1 | 6/2002 | Crank et al. |
| 2002/0173689 A1 | 11/2002 | Kaplan |
| 2003/0032929 A1 | 2/2003 | McGuckin, Jr. |
| 2003/0130575 A1 | 7/2003 | Desai |
| 2003/0149440 A1 | 8/2003 | Kammerer et al. |
| 2003/0161824 A1 | 8/2003 | Rackley et al. ............... 424/125 |
| 2003/0171644 A1 | 9/2003 | Anderson et al. |
| 2003/0176762 A1 | 9/2003 | Kammerer |
| 2003/0187382 A1 | 10/2003 | Unsworth |
| 2003/0216693 A1 | 11/2003 | Mickley |
| 2004/0002647 A1 | 1/2004 | Desai |
| 2004/0039338 A1 | 2/2004 | Lee et al. |
| 2004/0064098 A1 | 4/2004 | Cuschieri et al. |
| 2004/0068242 A1 | 4/2004 | McGuckin, Jr. |
| 2004/0092865 A1 | 5/2004 | Flaherty et al. |
| 2004/0097974 A1 | 5/2004 | De Leval |
| 2004/0106845 A1 | 6/2004 | Anderson et al. |
| 2004/0106846 A1 | 6/2004 | Gellman |
| 2004/0176726 A1 | 9/2004 | Katoh et al. |
| 2004/0260240 A1 | 12/2004 | Beyerlein |
| 2005/0004563 A1 | 1/2005 | Racz et al. |
| 2005/0065395 A1 | 3/2005 | Mellier |
| 2005/0101909 A1 | 5/2005 | Rossi |
| 2005/0113686 A1 | 5/2005 | Peckham ..................... 600/431 |
| 2005/0245787 A1 | 11/2005 | Cox et al. |
| 2005/0255039 A1 | 11/2005 | Desai |
| 2005/0261667 A1 | 11/2005 | Crank et al. |
| 2006/0025720 A1 | 2/2006 | Sawa et al. |
| 2006/0064062 A1 | 3/2006 | Gurusamy et al. |
| 2006/0129101 A1 | 6/2006 | McGuckin, Jr. |
| 2006/0135915 A1 | 6/2006 | Tucker |
| 2006/0135916 A1 | 6/2006 | Tucker |
| 2006/0189940 A1 | 8/2006 | Kirsch |
| 2006/0199990 A1 | 9/2006 | Rioux et al. ..................... 600/3 |
| 2006/0206116 A1 | 9/2006 | Yeung |
| 2006/0247600 A1 | 11/2006 | Yeung et al. |
| 2006/0265043 A1 | 11/2006 | Mandrusov et al. |

FOREIGN PATENT DOCUMENTS

| | | |
|---|---|---|
| WO | WO 96/16606 | 6/1996 |
| WO | WO 2006/027549 A1 | 3/2006 |

OTHER PUBLICATIONS

Medtronic Therapy/EP Systems, Transseptal Sheaths/Needles, http://www.medtronic.com/epsystems/trans_sheaths_needles.html, retrieved Jan. 2, 2007, 4 pages.

International Preliminary Report on Patentability, dated Jan. 19, 2012, for International Patent Application No. PCT/US2010/040341, from the International Bureau of WIPO.

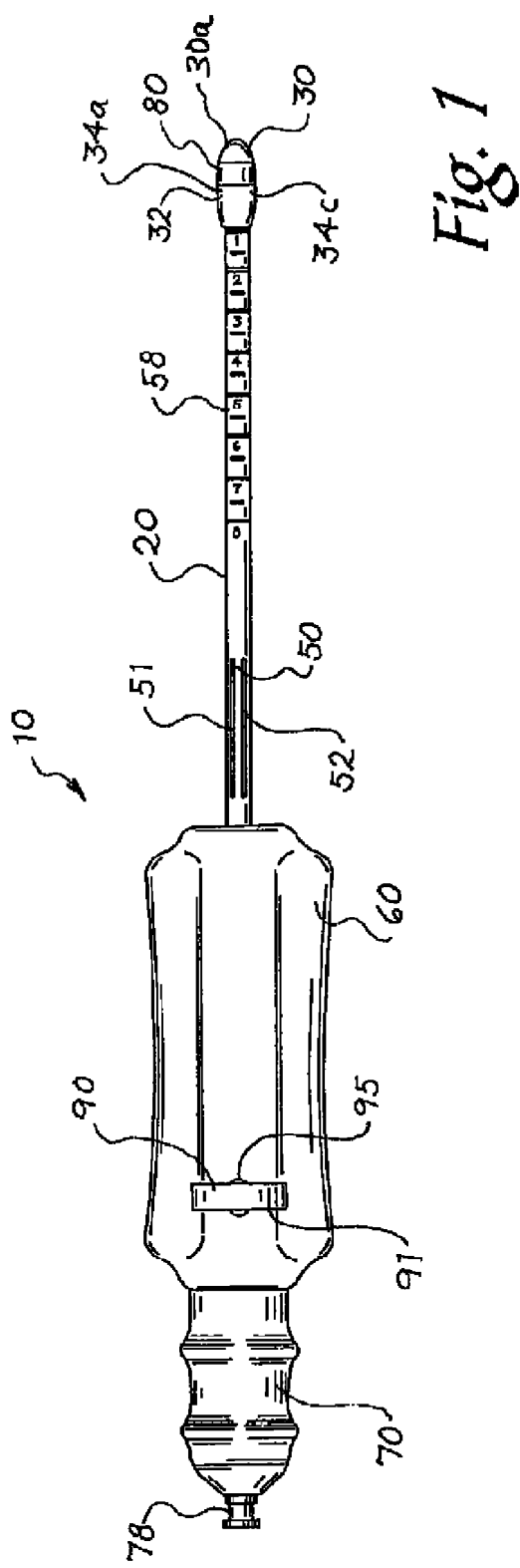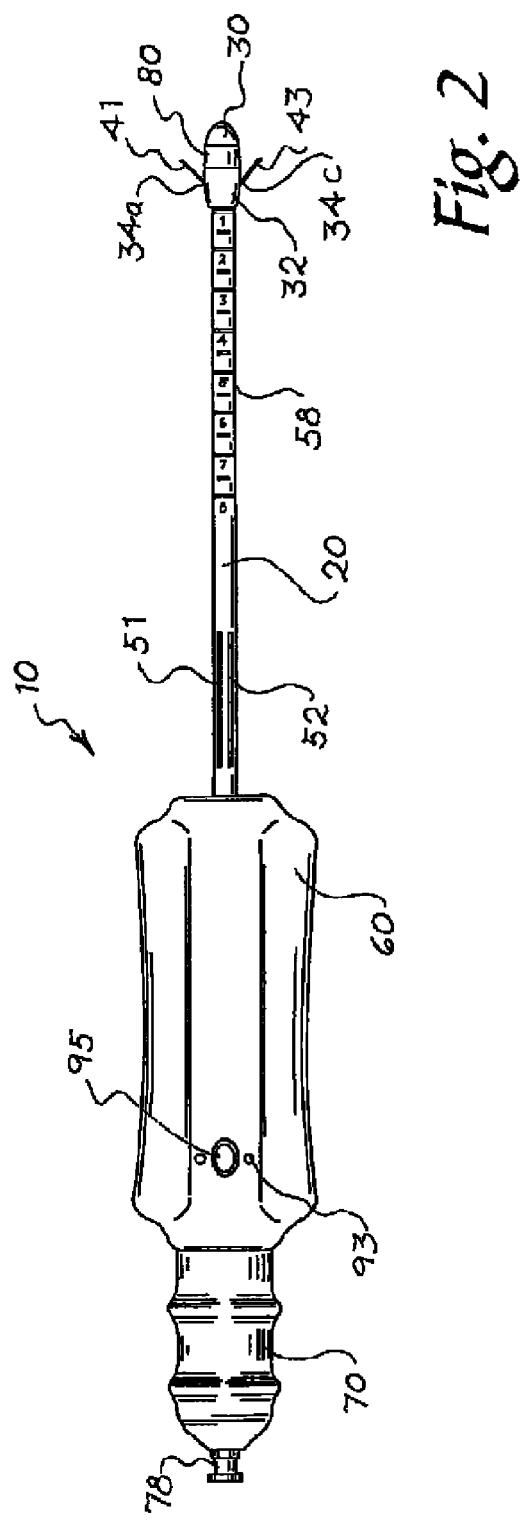
Fig. 1
Fig. 2

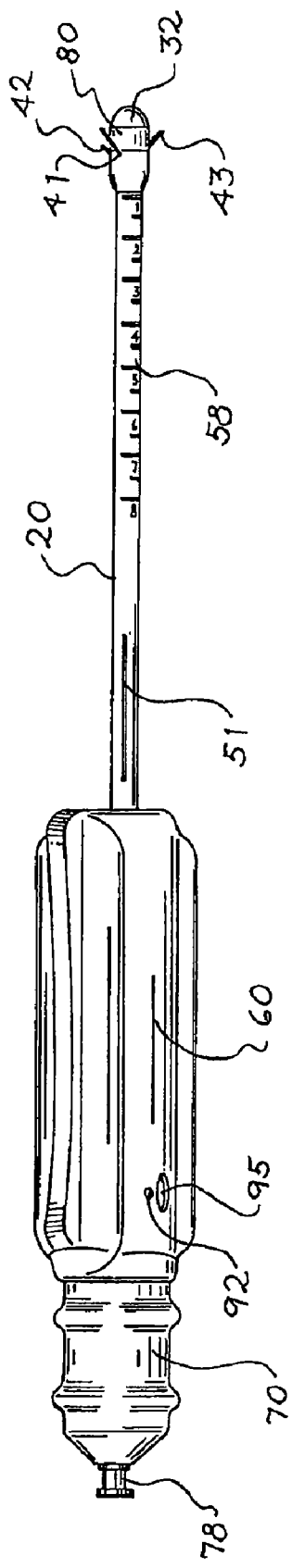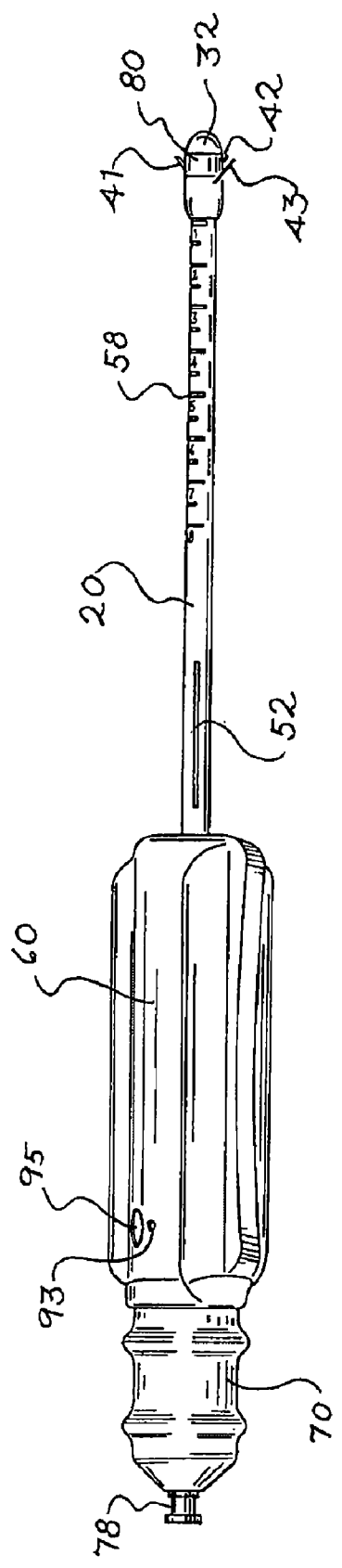

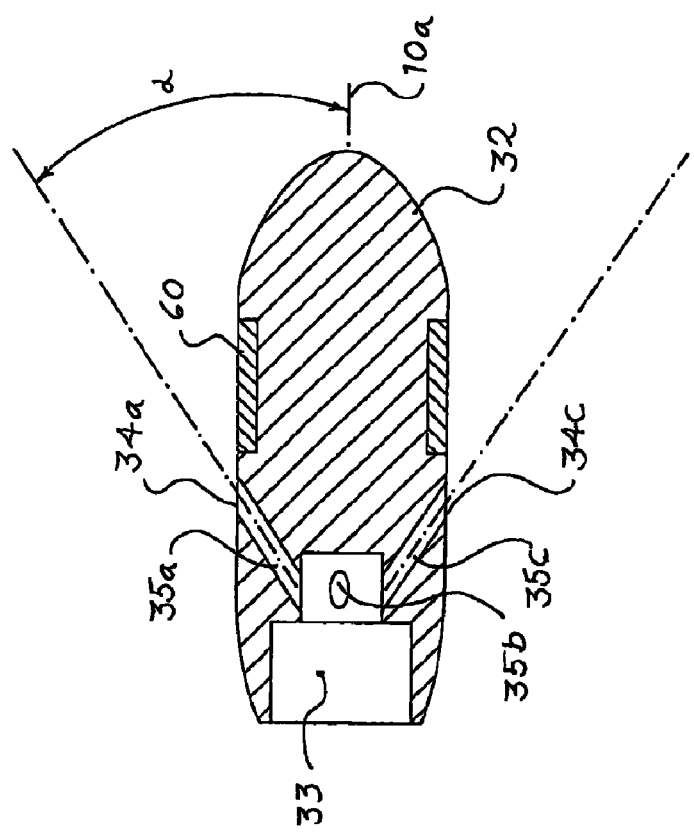
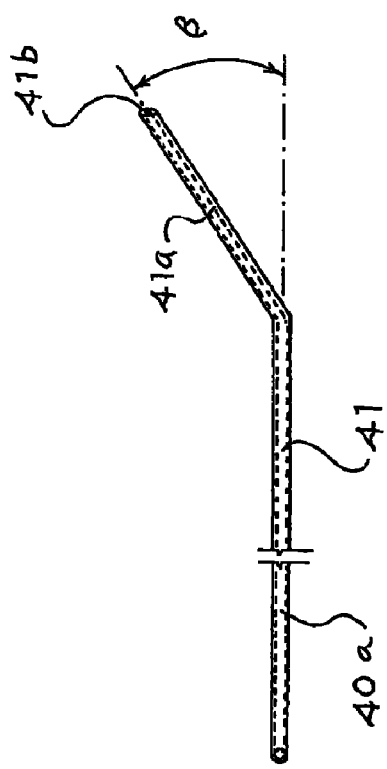
Fig. 7
Fig. 8

FLUID INJECTION DEVICE

TECHNICAL FIELD

Stress Urinary Incontinence ("SUI") is a urological disorder that exists in relatively large numbers of the human population and typically exists for older patients. Patients suffering from SUI often are unable to control and prevent the release of urine from their urethra, specifically in times of coughing, sneezing, laughing, or exercise. SUI may be caused by the weakening of muscle tissues, such as muscle tissues and fascia that coaxially surrounds the urethra, as well as weakening of bladder tissues, or a weakening or malfunction of the sphincter muscles at the bladder neck. Female patients have been known to suffer from SUI post pregnancy and delivery, after menopause, just prior to menstruation, and post several other urological surgical procedures. Several treatments are known for treatment to eliminate or minimize the effects of SUI, such as installing a pessary into the female patient's vagina, installing a urethral sling into a patient, or injecting bulking agents into the patient's tissue surrounding the urethra.

BRIEF SUMMARY

A first representative embodiment of the disclosure is provided. The embodiment includes an elongate cannula comprising a distal end portion, a proximal end portion, and a lumen defined therethrough, an outer circumferential surface defining an upper portion, a right side portion, a bottom portion, and a left side portion each substantially equally spaced from their respective neighboring portion around the circumferential surface of the cannula. The cannula additionally includes a plurality of apertures disposed through the distal end portion to provide communication from the lumen and a first of the plurality of apertures disposed on the right side portion, a second of the plurality of apertures disposed on the bottom portion, and a third of the plurality of apertures disposed on the left side portion. The cannula additionally includes a visually perceptible indicator that is configured to allow the cannula to be positioned at an appropriate rotational position within the patient. The device additionally includes a plurality of injection needles disposed within the lumen, each comprising a distal portion disposed in alignment with one of the first, second, and third apertures and a proximal end portion. The device additionally includes a first handle fixed with respect to the cannula and a second handle disposed in conjunction with the first handle and fixed to the proximal portion of each of the plurality of needles. The first handle is translatable with respect to the second handle to translate the plurality of needles from a first position where the distal portions of each of the plurality of needles are disposed within the lumen of the cannula, and a second position where the distal portion of each of the plurality of needles extends out of the lumen through their respective aperture.

Another representative embodiment of the disclosure is provided. The disclosure provides a method of treating stress urinary incontinence. The method includes the steps of providing a device with an elongate cannula with a plurality of apertures disposed upon a distal end thereof, and disposed upon right, bottom, and left sides of an outer circumferential surface of the cannula. The device includes a plurality of needles that each extend through a lumen in the cannula and selectively extend from each of the plurality of apertures. A handle is manipulable to urge the plurality of needles to extend outward from the apertures, and a visually perceptible indicator is disposed upon the cannula and configured to allow the user to align the device at the appropriate rotational position. The method additionally includes the steps of inserting the device into the patient with the visually perceptible indicator aligned in a first position, and manipulating the handle to extend the plurality of needles through the apertures. The method additionally further includes the steps of expelling fluid from the plurality of needles, retracting the plurality of needles into the cannula, and rotating the device to a second rotational position to move the visually perceptible indicator into a second different position, and extending the plurality of needles through the apertures and expelling additional fluid from the plurality of needles.

Yet another representative embodiment of the disclosure is provided. The disclosure provides a medical device for treating female stress urinary incontinence The device includes an elongate cannula comprising a distal end portion, a proximal end portion, and a lumen defined therethrough, an outer circumferential surface defining an upper portion, a right side portion, a bottom portion, and a left side portion each substantially equally spaced from their respective neighboring portion around the circumferential surface of the cannula, the cannula further comprising a plurality of apertures disposed through the distal end portion to provide communication from the lumen, a first of the plurality of apertures disposed on the right side portion, a second of the plurality of apertures disposed on the bottom portion, and a third of the plurality of apertures disposed on the left side portion, wherein there are no apertures disposed upon the upper portion. A plurality of injection needles are disposed within the lumen, each needle includes a distal portion disposed in alignment with one of the first, second, and third apertures and a proximal end portion. A first handle is fixed with respect to the cannula and a second handle is disposed in conjunction with the first handle and fixed to the proximal portion of each of the plurality of needles. The first handle is translatable with respect to the second handle to translate the plurality of needles from a first position where the distal portions of each of the plurality of needles are disposed within the lumen of the cannula, and a second position where the distal portion of each of the plurality of needles extends out of the lumen through their respective aperture.

Advantages of the present disclosure will become more apparent to those skilled in the art from the following description of the preferred embodiments of the disclosure that have been shown and described by way of illustration. As will be realized, the disclosed subject matter is capable of other and different embodiments, and its details are capable of modification in various respects. Accordingly, the drawings and description are to be regarded as illustrative in nature and not as restrictive.

BRIEF DESCRIPTION OF THE DRAWINGS

FIG. 1 is a top view of a fluid injection device with the plurality of needles in the first withdrawn position.

FIG. 2 is the view of FIG. 2 with the plurality of needles in the second extended position.

FIG. 3a is the view of FIG. 1 depicting the device rotated such that the second alignment marker is aligned vertically with the cannula.

FIG. 3b is the view of FIG. 3a depicting the device rotated in the opposite direction such that the third alignment marker is vertically aligned with the cannula.

FIG. 7 is a cross-sectional view of the bulb of the device of FIG. 1.

FIG. 8 is a side view of a needle of the device of FIG. 1.

DETAILED DESCRIPTION

Figure 4:
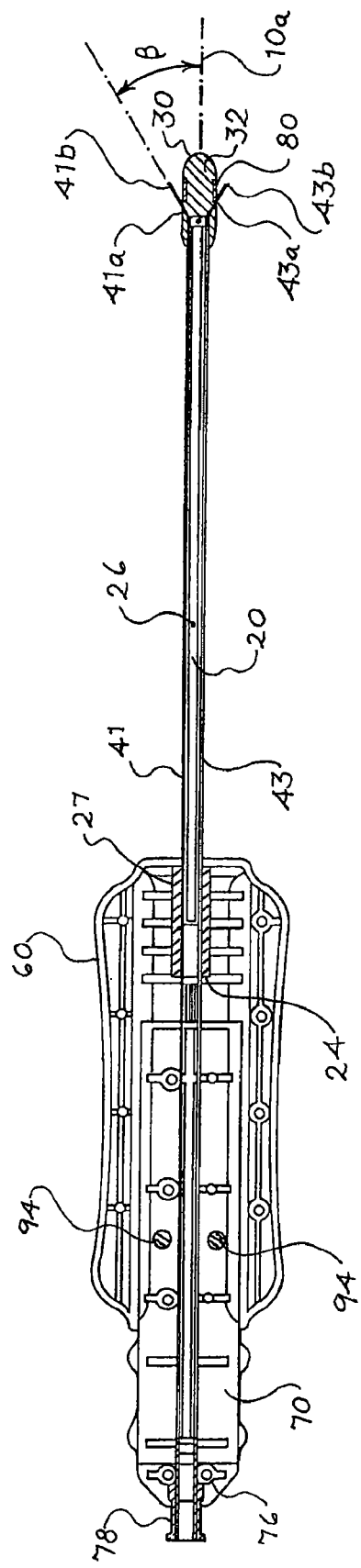
FIG. 4 is a cross-sectional view of the device showing the plurality of needles in the extended position.

Turning now to FIGS. 1-9, a fluid injection device 10 suitable for various medical procedures is provided. In some embodiments, the device 10 may be suitable for injecting therapeutic agents, such as bulking agents, stem cell based media or agents, or other injection media, into the tissue coaxially surrounding a female urethra in an attempt to strengthen and bulk the tissue therein to prevent or reduce the effects of stress urinary incontinence. In other embodiments, the device 10 may be used in other portions of the human or mammal anatomy to inject therapeutic agents simultaneously at multiple predetermined or reliable locations within the patient. The device 10 is configured to be inserted into a patient through an available orifice, such as directly into the female urethra, or the device 10 may be inserted into the patient percutaneously. As can be appreciated, the embodiment discussed in detail below is configured for insertion in the patient's urethra, but the device 10 can be otherwise sized and shaped to be specifically configured for other anatomical locations and procedures without departing from the scope of this disclosure.

The device 10 includes an elongate relatively flexible cannula 20, a first handle 60 that is fixed to a portion of the cannula 20, and a second handle 70 that is movably disposed with respect to the first handle 60. A plurality of needles 41, 42, 43 are movably disposed within a lumen 26 of the cannula 20 and are each fixed to the second handle 70. The first and second handles 60, 70 may be linearly translated with respect each other, which causes the plurality of needles 41, 42, 43 to translate within the lumen 26 of the cannula 20. The cannula 20 further includes a distal end portion 30 that includes a plurality of apertures 34a, 34b, 34c disposed therethrough to provide communication with the lumen 26. Each of the plurality of needles 41, 42, 43 are disposed within the cannula 20 to be aligned with a respective one of the plurality of apertures 34a, 34b, 34c. When the first and second handles 60, 70 are disposed in a first position (FIG. 1), the distal tips 41b, 42b, 43b of the respective plurality of needles 41, 42, 43 are disposed within the apertures 34a, 34b, 34c just inside of the outer circumferential surface of the cannula 20. When the first and second handles 60, 70 are linearly translated with respect to each other into a second position (FIGS. 2-4 and 9) the distal tips of each plurality of needles 41, 42, 43 extend outward from the apertures 34a, 34b, 34c and the outer circumferential surface of the cannula 20 to be interact with, and be inserted into tissue proximate to the distal end portion 30 of the cannula 20.

The cannula 20 is an elongate flexible member that spans between a distal end portion 30 and a proximal end portion 22. The cannula 20 includes a lumen 26 that spans from an open proximal end 22a upon the proximal end portion 22 to a closed distal tip 30a upon the distal end portion 30. In some embodiments, the distal end portion 30 may be made from a bulb 32 or closed tube that is connected to the distal end of the cannula 20. The bulb 32 (FIG. 8) includes a lumen 33 defined at the proximal end portion thereof that allows communication with the lumen 26 of the cannula 20 when the bulb 32 is fixed to the distal end of the cannula 20.

The apertures 34a, 34b, 34c are each disposed at various locations about the outer circumferential surface of the bulb 32. As best understood with reference to FIG. 6, the apertures 34a, 34b, 34c may be disposed at about the 3 o'clock position or right side position W, the 6 o'clock position or bottom position X, and the 9 o'clock position or left side position Y, respectively if the distal end of the bulb 32 is considered to be the face of a conventional analog clock. In some embodiments, the apertures are disposed such that no aperture is provided at about the 12 o'clock position or upper position Z (with continued reference to the view of FIG. 6). In some embodiments, the first and third apertures 34a, 34c are each disposed substantially equidistant from the second aperture 34b upon the outer circumferential surface of the bulb. In some embodiments, each of the positions W, X, Y, Z are spaced from their adjacent positions by about ninety degrees.

In other embodiments, the outer circumferential surface of the cannula 20 is divided into upper, right, bottom, and left quadrants, each quadrant covering about a fourth of the outer circumferential surface of the cannula 20. The quadrants may be aligned such that the border between neighboring quadrants is disposed about midway between upper Z and right side W position, between the right side W and bottom X position, between the bottom X and left side Y position, and between the left side Y and upper Z positions. In some embodiments, an aperture (e.g. 34a) is disposed upon the right quadrant, an aperture is disposed upon the bottom quadrant, and aperture is disposed upon the left quadrant, and no apertures are disposed upon the upper quadrant.

The apertures 34a, 34b, 34c are disposed upon the bulb 32 to accurately position the needles 41, 42, 43 projecting therefrom into a desired pattern from the bulb 32. In embodiments where the device 10 is contemplated to be used to inject bulking solution or other therapeutic agents into the muscular tissue surrounding a female patient's urethra for the treatment of or prevention of stress induced incontinence, it is often necessary that fluid not be injected into through the anterior portion of the urethra (i.e. the portion of the urethra that runs closest to the front of the body) because blood vessels and nerve bundles are disposed proximate to the urethra in this area. Accordingly, the bulb 32 upon the cannula 20 is configured with apertures at three (or other numbers of multiple locations) locations for needles 41, 42, 43 to exit the cannula 20 to substantially simultaneously enter the tissue (submucosa and musculature) coaxially surrounding the urethra but remote from the upper portion of the urethra. Once the needles pierce and are positioned within the tissue the device 10 can be manipulated to simultaneously inject therapeutic agents into the muscle tissue while avoiding injection into the upper portion of the urethra.

The plurality of apertures 34a, 34b, 34c are each fluidly connected to the lumen 33 of the bulb 32 (and ultimately to the lumen 26 of the cannula 20) with respective angled sublumens 35a, 35b, 35c that each provide for transmission of one of the plurality of needles (discussed below) disposed therethrough. In some embodiments, each of the sublumens may be disposed at an acute angle α with respect to the longitudinal axis 10a of the device at the distal end portion 30 of the cannula 20. For example, in some embodiments, the sublumens 35a, 35b, 35c may be disposed at an angle α of about 35 degrees, 40 degrees, 45 degrees to the longitudinal axis 10a, or other appropriate angles within the range of about 20 degrees to about 60 degrees with respect to the longitudinal axis 10a.

A plurality of elongate injection needles, in some embodiments, first, second, and third needles 41, 42, 43, are movably disposed within the lumen 26 of the cannula 20 and the bulb 32, where provided. As shown in FIG. 8, each needle 41, 42, 43 includes a lumen 40a along its length to allow liquid, such as therapeutic agents, to flow therethrough and exit the respective needle 41, 42, 43 through a tip 41b, 42b, 43b thereon. In some embodiments, the tips 41b, 42b, 43b may include a sharpened point thereon and a beveled edge that allows the tip 41b, 42b, 43b to easily pierce the patient's tissue with movement or force applied to the needle 41, 42, 43 by the device 10, and specifically the relative movement of the second handle 70 while the first handle 60 is held stationary. The distal end portions 41a, 42a, 43a of the needles are configured to be disposed within the respective sublumens 35a etc. of the bulb 32, with the tip 41b, 42b, 43b of each needle 41, 42, 43 disposed just below the outer circumferential surface of the bulb 32 when the device 10 (and handles 60, 70) are in the first position. When the first and second handles 60, 70 are transferred toward and reach the second position, the tips 41b, 42b, 43b and distal end portions 41a, 42a, 43a of the plurality of needle 41, 42, 43 each simultaneously extend from and out of the respective apertures 34a, 34b, 34c upon the bulb 32.

The distal end portions 41a, 42a, 43a of each of the needles 41, 42, 43, respectively, each may be configured to be curved or bent with respect to the remainder of the needle. In some embodiment, the distal end portions 41a, 42a, 43a may each be bent or angled to form an acute angle β with respect to the proximal and central portions of the respective needle. In some embodiments, the angle β may be about 40 degrees, about 20 degrees, about 30 degrees, or at suitable angles within the range of about 20 and about 60 degrees. In some embodiments, the bend angle β of the distal end portion of the respective needle 41, 42, 43 may be substantially the same as the angle α that the respective sublumens 35a, 35b, 35c form of the bulb with respect to the longitudinal axis 10a of the cannula 20 through the bulb 30. In other embodiments, the angles α and β may be slightly different, such as an embodiment specifically depicted in the figures showing the sublumen angle of about 35 degrees and a bend angle of the needle of about 40 degrees. In this embodiment (and other embodiments where the angles α and β are not exactly the same), the needle presses or moves against at least a portion of the inner surface of the respective sublumen 35a, 35b, 35c (see FIG. 7), which increases the friction between the needle and the bulb, therefore preventing unintended motion of the needles within the cannula due to unintended external forces placed thereon. The plurality of needles 41, 42, 43 may be made from strong and flexible materials capable of being configured with a lumen and capable of maintaining a sharpened tip. In some embodiments, the needles 41, 42, 43 may be stainless steel, while in other embodiments the needles may be Nitinol or various alloys thereof.

The first handle 60 is disposed to surround and enclose the proximal end portion 24 of the cannula 20 and fixed thereto to prevent relative motion between the cannula 20 and the first handle 60. In some embodiments, the first handle 60 is formed from two clamshell halves (see FIG. 5) that are fixed together to surround the proximal end portion 24 of the cannula 24. In some embodiments, the cannula 20 includes a noncircular portion 27 that is placed within a specific molded portion 67 of the first handle 60 to enclose and longitudinally fix the two together.

The second handle 70 is disposed to allow relative linear motion between the first and second handles 60, 70. In some embodiments, the second handle includes a cylindrical portion 74 that includes an outer diameter just smaller than an inner diameter of a lumen 64 defined by the first handle to allow the second handle 70 to be slid for a specific distance within and with respect to the first handle 60. In some embodiments, the second handle 70 may include a slot 77 (FIG. 5) that receives a projection (not shown) extending inward from the first handle 60. The length of the slot 77 defines the potential length of travel of the projection therein and accordingly, the range of relative longitudinal motion between the first and second handles 60, 70, and the distance that the plurality of needles extend from their respective apertures 34a, 34b, 34c in the cannula when the handles are in the second position.

The second handle 70 may receive a luer lock adaptor 78 upon the proximal end 76 thereof. The adaptor 78 is is configured to receive a luer lock fitting from an external source of therapeutic fluid attached thereto with a conventional luer thread engagement device. The proximal ends of each of the needles 41, 42, 43 are passed through holes formed in the luer lock adaptor 78 and glued (or otherwise fixed) thereto to fix the needles 41, 42, 43 to the second handle 70. The open proximal tips of each needle 41, 42, 43 extend into the luer lock adaptor 78 such that fluid that passes into the adaptor 78 from an external source of fluid flows into the lumen of each needle 41, 42, 43 and ultimately from the tip 41b, 42b, 43b of each needle. The second handle 70 may be formed from two clamshell halves. As discussed herein, relative movement of the first and second handles 60, 70 causes the needles 41, 42, 43 to translate within with cannula 20 and selectively extend from or retract within the apertures 34a, 34b, 34c within the bulb 32.

Figure 5:
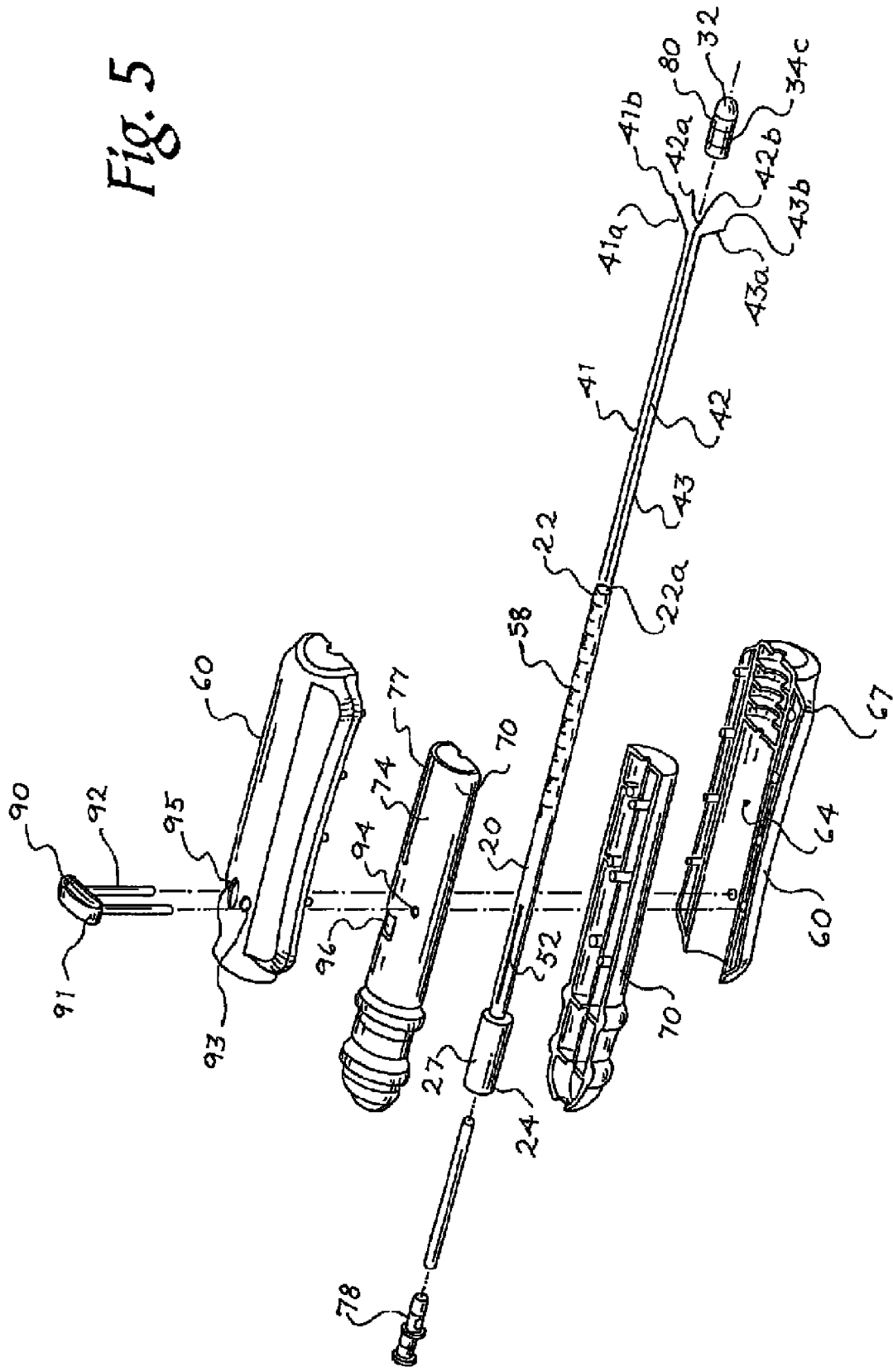
FIG. 5 is an exploded view of the device of FIG. 1.
Figure 6:
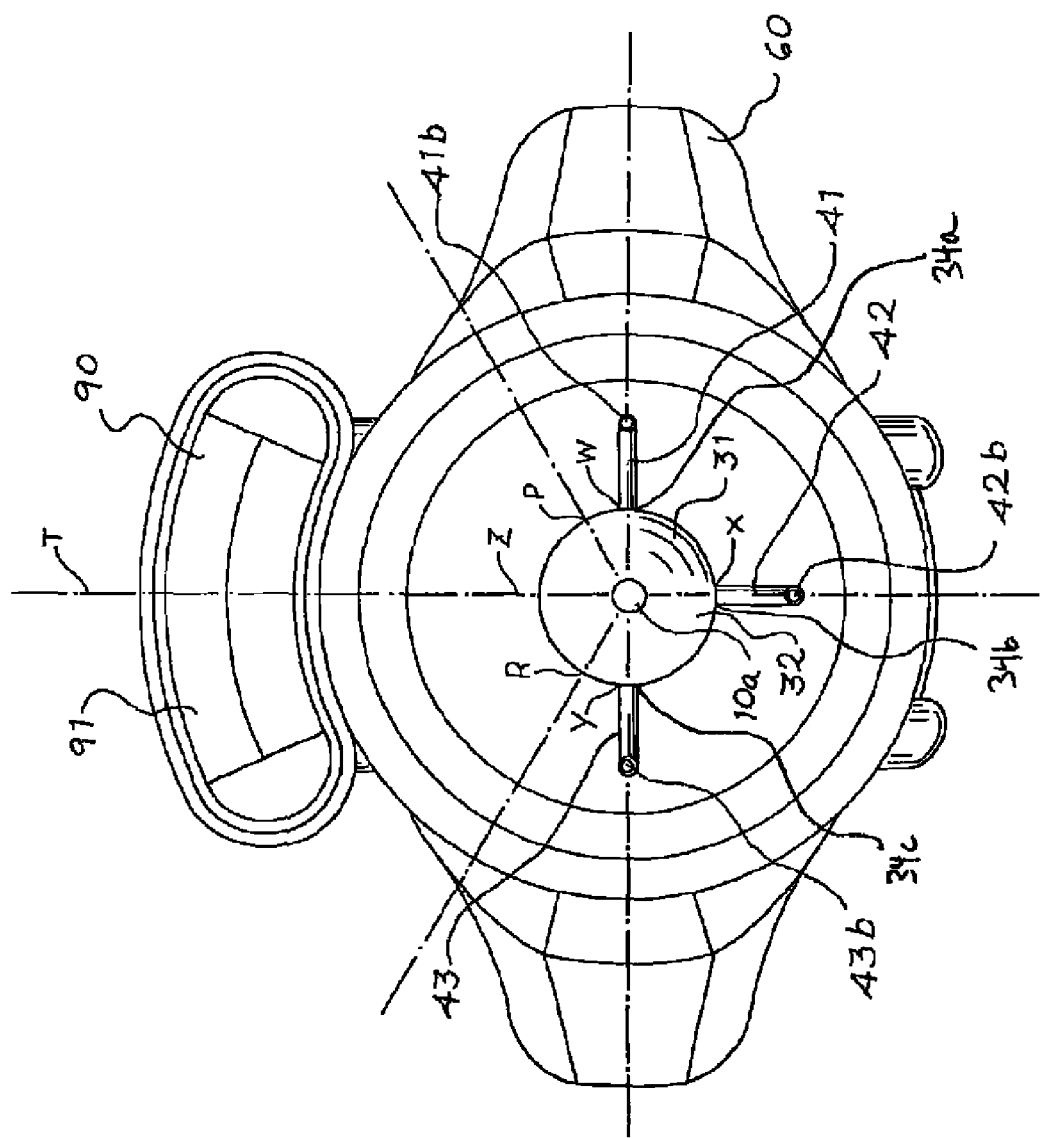
FIG. 6 is a front view of the device of FIG. 1 showing the plurality of needles in the extended position.
Figure 9:
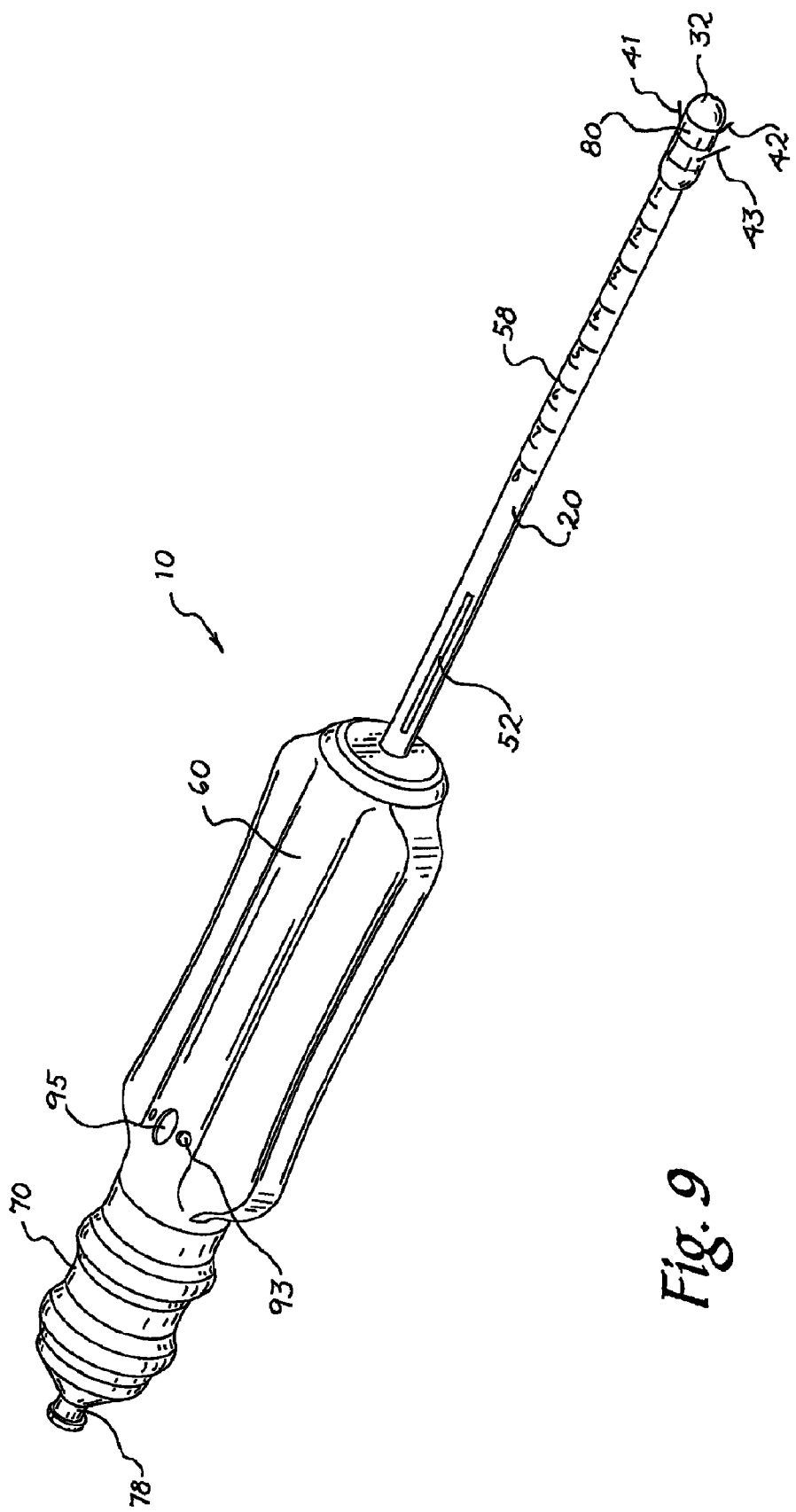
FIG. 9 is a perspective view of the device of FIG. 1 with the plurality of needles in the extended position.

As shown in FIGS. 1 and 5, the first and second handles 60, 70 may include a lock 90 that may be selectively engaged to maintain the first and second handles 60, 70 in the first position (FIG. 1) with the needle tips 41b, 42b, 43b retracted within the bulb 32. The lock 90 may include a removable locking member 91 that includes one or more elongate posts 92. Each of the first and second handles 60, 70 may include holes 93, 94, respectively, with an inner diameter slightly larger than the outer diameter of the posts 92. When the first and second handles 60, 70 are in the first position, the holes 93, 94 are coaxially aligned to allow the posts 92 to be received through the holes 93, 94 in the first and second handles, which prevents relative motion of the first and second handles 60, 70. The lock 90 is useful to maintain the device 10 in the first position (with the plurality of needles retracted into the cannula 20) for periods of non-use to avoid inadvertent piercing of the user by the needles 41, 42, 43 which could cause injury, damage to the needles, or loss of sterilization of the needles 41, 42, 43. The lock 90 is also beneficial because it allows the cannula 20 of the device 10 to be inserted and properly positioned within the patient, while insuring that the needles 41, 42, 43 do not accidentally extend from the cannula 20 and penetrate the patient's tissue at incorrect locations or at an inappropriate time for the procedure.

The lock may be disengaged by removing the locking member 91 from the holes 93, 94, which allows relative longitudinal movement between the first and second handles 60, 70. In other embodiments, different types of locks 90, such as a pivotable or movable member rotationally or longitudinally fixed to one of the handles 60, 70 that may be moved to selectively engage and disengage the other of the first and second handles 60, 70.

The first and second handles 60, 70 may additionally provide a visual indication that the second handle 70 has reached the second position with respect to the first handle 60 and the needles 41, 42, 43 are fully extended from the bulb 32. The first handle 60 may include a second aperture 95 that allows the surface of the second handle 70 to be viewed therethrough. The second handle 70 may include a visual indication, such as a painted, etched, or otherwise treated mark 96 that aligns in registry with the second aperture 95 when the handles are in the second position. Both the first and second handles 60, 70 may be formed with sizes and shapes to be ergonomically held and manipulated by the user. The first and second handles 60, 70 may each be formed with two identical clamshell halves (i.e. both halves with the same shape and features) such that the same part can be used twice to form the respective handle, increasing the efficiency of the assembly process and minimizing the number of different parts necessary to assemble the device 10.

The cannula 20 may include a visually perceptible indicator 50 thereon that allows the physician to properly position the device 10 at the proper rotational angle within the patient when inserted into the appropriate depth, as discussed below. The visually perceptible indicator 50 may include one or two lines 51, 52 painted, etched, coated, scribed, or otherwise marked or disposed upon an outer surface of the cannula 20. In other embodiments, the first and second lines 51, 52 may be or include tactile features upon the outer circumferential surface of the cannula, such as indentations, ridges, roughened areas, areas of differing material, relatively "sticky" regions, and the like such that the physician can tactilely feel the lines and align the device 10 with respect to the lines without viewing the lines 51, 52.

The lines 51, 52 are disposed in parallel to the longitudinal axis 10a of the cannula 20 and disposed upon a relatively proximal location of the cannula 20 that normally extends out of the patient when the device is properly inserted for use. In some embodiments, the first and second lines 51, 52 may be disposed on opposite sides of a vertical plane T (FIG. 6, front view of the device) that extends through the longitudinal axis 10a of the cannula 20 and through each of the 12 and 6 o'clock positions Z, X. In some embodiments, the first and second lines 51, 52 may be equally spaced on opposite sides of the plane T, such as the first line 51 being substantially equally spaced between the 12 and 3 o'clock positions, Z, W and the second line being substantially equally spaced between the 12 and 9 o'clock positions Z, Y. In other embodiments, the first and second lines 51, 52 may be positioned at about the 2 o'clock position P and the 10 o'clock position R (FIG. 6), respectively. In other embodiments, the visual perceptible indicator 50 may include only one of the first or second lines 51, 52, positioned at one of the locations for that line discussed above.

The first and second lines 51, 52 are disposed upon the cannula 20 such that the device 10 is normally inserted into the patient while in the lithotomy position with the two lines 51, 52 (when both provided) extending on substantially equal and opposite sides of the plane T (or top portion of the outer circumferential surface of the cannula 20) when viewed from above (or from the view of FIG. 2). When the physician views the first and second lines 51, 52 in this orientation from above, the physician can be confident that the apertures 34a, 34b, 34c in the bulb are aligned to inject their respective needles 41, 42, 43 into the desired locations (and away from the vessels and nerves proximate the urethra).

The first and second lines 51, 52 are additionally positioned upon the cannula 20 so that the cannula 20 can be additionally be rotated to two other "safe" positions (i.e. where the needles 41, 42, 43 will inject into different rotational portions of tissue surrounding the urethra but still avoid the vessels and nerves proximate the urethra) where second and third injections can be made into different locations within the tissue surrounding the urethra without having to remove and reinsert the device into the patient. Specifically, after the first injection is made (with the device 10 oriented as shown in FIG. 2), the needles 41, 42, 43 may be withdrawn into the lumen 26 of the cannula 20 (by withdrawing the second handle 70 to the first position with respect to the first handle 60 (FIG. 1)), and then rotating the device 10 (while holding the first handle 60 stationary to prevent longitudinal motion of the cannula 20 within the patient) until first line 51 is aligned with a vertical plane through the longitudinal axis 10a of the cannula 20 (when viewed from above and shown in FIG. 3a). In other words, the device 10 is rotated until the first line 51 is disposed upon the top circumferential outer surface of the cannula 20 when viewed from above. In this rotated orientation, the needles 41, 42, 43 may be simultaneously expelled from the cannula 20 and bulb 32 and a second dose of therapeutic fluid injected into the tissue surrounding the urethra simultaneously. A third injection may be made into the patient by withdrawing the needles 41, 42, 43 again into the cannula 20 and rotating the device 10 in the opposite direction until the second line 52 is disposed within the vertical plane as referenced above and shown in FIG. 3b. The needles 41, 42, 43 may again be expelled from the cannula 20 and yet additional therapeutic fluid injected into the patient's tissue proximate the urethra. As can be understood, the properly aligned device can be effectively and precisely operated in one of the rotational positions shown in FIGS. 2-3b, in two of those positions, or in all three of those positions depending upon the number of injections necessary for effective treatment, with the needles 41, 42, 43 being clear of the vessels and nerves proximate the urethra.

As understood, the selected positioning of the first and second lines 51, 52 into the three rotational positions discussed above (and depicted in FIGS. 2-3b) allows nine separately spaced injections of therapeutic fluid into the desired tissue surrounding the urethra in a simple and quick procedure, with the physician having confidence that the injection sites of the needles remain sufficiently away from the vessels and nerves positioned proximate the urethra. The configuration of the device 10 to allow the physician to rely on the position of the visually perceptible indication 50 upon the cannula 20 is additionally beneficial because it allows the physician to hold and manipulate the first and second handles 60, 70 in any way that is comfortable for them without having to rely on any alignment markings or tactile features on disposed on the handles 60, 70, which removes any manufacturing requirement for tight or precise rotational and longitudinal tolerances between the first handle 60 and the cannula 20. This allows the physician to concentrate their vision upon the cannula 20 at a location closer to the injection site than would be possible if observation of the handle 60 was necessary for proper positioning. The first and second lines 51, 52 also allow the device 10 to be repositioned to two independent positions quickly and reliably for three successive applications of therapeutic agents without removing the device 10 from the patient.

The device 10 may include one or more depth alignment guides configured to allow the physician to accurately position the device 10 within a patient by inserting the device 10 to the desired penetration depth for the procedure. In some embodiments, the bulb 32 (or distal end of the cannula 20 when no bulb 32 is provided) may include an imaging band 80, such as an echogenic band or a radiopaque band, disposed around the outer circumferential surface thereof. In some embodiments, the imaging band 80 may be made from any material that is visually or otherwise perceptible by the physician when the device 10 is inserted into the patient. The imaging band 80 may be configured to be detected by ultrasound equipment, x-ray, fluoroscopy, or other relatively non-invasive imaging or detection techniques.

The imaging band 80 may be positioned just forward of the plurality of apertures 34a, 34b, 34c disposed upon the bulb 32 and spaced from the apertures such that the tips 41b, 42b, 43b of the respective needles are aligned with the longitudinal center of the imaging band 80 when the needles 41, 42, 43 are fully extended from the cannula 20 (FIGS. 2-4). The necessary spacing of the imaging band 80 from the apertures 34a, 34b, 34c will be understood to be a function of the angle β that the distal end portions 41a, 42a, 43a make with respect to the longitudinal axis 10a of the cannula 20 when exiting the cannula 20 as well as the length of the needles 41, 42, 43 that exit the bulb 32. As an example, in one embodiment the length of the distal end portion 41a, 42a, 43a of the needles exiting the cannula 20 is about 7 mm and the needles each exit at about a 40 degree angle. In this embodiment, the center of the imaging portion is disposed about 5.4 mm in front of each of the apertures 34a, 34b, 34c.

The device 10 where the imaging band is an echogenic band 80 configured to be monitored with an ultrasound system during insertion and placement to ensure that the device 10 and specifically the distal end portion 30 of the device 10 is aligned as necessary with respect to the length of the patient's urethra to precisely inject the therapeutic fluid into the desired position within the patient. The ultrasound may be a conventional ultrasound system, including a sensor or probe for external ultrasound monitoring, a processor, an input device, and a display to depict the ultrasound image for observation by the physician during the procedure.

In some embodiments, the cannula 20 may include a plurality of depth markings 58 disposed thereon that provide a visual indication of the insertion depth of the cannula 20 when viewing the portion of the cannula 20 extending outward from the patient. In some embodiments, the depth markings 58 may be calibrated to show the depth from the centerline of the echogenic portion 80 (which is the approximate longitudinal position of the tips 41b, 42b, 43b of the needles 41, 42, 43 when fully extended from the cannula 20) while in other embodiments, the depth markings 58 may be calibrated with respect to the proximal end of the echogenic portion 80, or based upon the location of the apertures 34a, 34b, 34c upon the distal end portion 30, or another suitable calibration scheme. Accordingly, the physician may visually monitor the depth markings 58 upon the cannula 20 to independently verify the correct positioning of the device 10 either when an ultrasound system is not available, or as a backup indication to the ultrasound system.

In embodiments where the device 10 is intended to inject therapeutic fluid into the female urethra, for example for the treatment of Stress Urinary Incontinence, it has been found that the average adult female's urethra is about 3.5 cm in length and best results are achieved when the device 10 is positioned within the urethra to inject treatment fluid therein at about 2.5 cm into the urethra. Accordingly, in devices 10 that include depth markings 58, the device 10 may be inserted into the patient until the 2.5 cm marking is just visible to the physician. Alternatively, or additionally, in embodiments where the device 10 is provided with an echogenic portion 80, the device 10 may be positioned at the appropriate position with the patient's urethra under guidance of the ultrasound system based on the physician's knowledge of the specific patient's anatomy and experience at interpreting the display of an ultrasound system.

The average female urethra has an initial submucosa layer that defines the inner surface of the lumen of the urethra that has been noted in some patients to be about 1.5-3 mm thick. A layer of muscle tissue is disposed coaxially outboard of the submucosa. It has been experimentally determined that the therapeutic fluid is best injected into the mid thickness of the muscle tissue for best results in treating SUI when using therapeutic fluids derived form autologous muscle-derived stem cells (discussed below). In these embodiments, the device 10 may be configured such that the tips 41b, 42b, 43b of the needles 41, 42, 43 each extend about 4.5 mm to about 5.0 mm from the outer circumferential surface of the cannula 20 in the radial direction, which is a depth experimentally determined to inject therapeutic fluid into an appropriate location of muscle tissue, at least for some patients. As can be understood, the lengths of the needle (and the length of their extension from the cannula 20) may be altered within the scope of this disclosure depending on the experimentally determined (or otherwise obtained) average depth and thickness of the patient's urethral muscle tissue. For example, the needles 41, 42, 43 may be configured to extend 3.0 mm, 4.0 mm, 5.0 mm, 6.0 mm, 7.0 mm or other suitable distances radially from the cannula and into the patient's muscle tissue It has also been experimentally determined that the therapeutic fluid is best injected into the submucosa tissue when collagen or other bulking agents are injected into the patient. In some embodiments, the needles 41b, 42b, 43b may be otherwise sized to extend 1.5, 2.0, 2.5, 3.0, or 3.5 mm (or other known lengths corresponding to the urethral submucosa tissue in the relevant population) to inject the therapeutic fluid into the patient's submucosa tissue. In some embodiments, the needles may be sized to extend a depth within the range of about 2.5 mm to about 9 mm. In embodiments where the device 10 is configured for injecting therapeutic agents into other portions of the patient's anatomy, the radial depth of injection may be different depending on the desired location.

In some embodiments, the device 10 may be configured to be inserted into male patient's urethra to inject therapeutic fluid therein for treatment of male SUI or for other types of treatment. In these embodiments, the sizes listed herein for the female device would be modified to provide a suitable device for injecting into the male urethra. For example, the male urethra is significantly longer than the female urethra so the overall length of the device would be increased. In some embodiments, the cannula 20 may be more flexible than the cannula 20 in the female device to allow the cannula for the male device to travel the relatively tortuous curved path through the male urethra. Similarly, in some embodiments, the cannula of the male device may be precurved to allow the cannula to easily navigate the male urethra to the location for injection. In still other embodiments, the device 10 may be configured to inject therapeutic fluid into other portions of the patients' urological system, such as the patient's prostate, bladder, or other suitable portions of the anatomy. One of skill in the art will appreciate with an understanding of the subject disclosure that the device 10 disclosed herein may be successfully modified as necessary to achieve the clinical treatment goal.

The device 10 may be configured to inject a variety of different therapeutic agents into patients. For example, the device 10 may be configured to inject bulking agents into the urethral tissue to increase the volume and density of the muscle tissue surrounding the urethra. For example, the therapeutic agent may be collagen or other fluids. In some embodiments, the therapeutic fluid may derived from autologous muscle-derived stem cells, or derived from adult stem cells obtained from other donors, either human donors or potentially mammals. Suitable stem cell therapies, including equipment, procedures, know how, supplies etc. are under development by and available from Cook MyoSite Incorporated, of Pittsburgh, Pa.

While the preferred embodiments of the disclosure have been described, it should be understood that the disclosure is not so limited and modifications may be made without departing from the disclosure. The scope of the invention is defined by the appended claims, and all devices that come within the meaning of the claims, either literally or by equivalence, are intended to be embraced therein.

What is claimed is:

1. A medical device comprising:
   an elongate cannula comprising a distal end portion, a proximal end portion, and a lumen defined therethrough, an outer circumferential surface defining an upper portion, a right side portion, a bottom portion, and a left side portion each substantially equally spaced from their respective neighboring portion around the circumferential surface of the cannula, the cannula further comprising a plurality of apertures disposed through the distal end portion to provide communication from the lumen, a first of the plurality of apertures disposed on the right side portion, a second of the plurality of apertures disposed on the bottom portion, and a third of the plurality of apertures disposed on the left side portion, and a visually perceptible indicator that is configured to allow the cannula to be positioned at an appropriate rotational position within a patient,
   wherein the visually perceptible indicator is a line applied to the outer circumferential surface of the cannula parallel to a longitudinal axis thereof and is disposed at a circumferential position such that a central axis of the line parallel to the longitudinal axis is disposed between the upper portion and one of the right or left side portions of the outer circumferential surface of the cannula;
   a plurality of injection needles disposed within the lumen, each comprising a distal portion disposed in alignment with one of the first, second, and third apertures and a proximal end portion; and
   a first handle fixed with respect to the cannula and a second handle disposed in conjunction with the first handle and fixed to the proximal end portion of each of the plurality of needles, the first handle translatable with respect to the second handle to translate the plurality of needles from a first position where the distal portions of each of the plurality of needles are disposed within the lumen of the cannula, and a second position where the distal portion of each of the plurality of needles extends out of the lumen through their respective aperture.

2. The medical device of claim 1, wherein the line comprises a first line parallel to the longitudinal axis and disposed at a circumferential position such that the central axis of the line parallel to the longitudinal axis is disposed between the upper portion and the right side portion of the outer circumferential surface of the cannula and a second line parallel to the longitudinal axis and disposed at a circumferential position such that the central axis of the line parallel to the longitudinal axis is disposed between the upper portion and the left side portion of the outer circumferential surface of the cannula.

3. The medical device of claim 2, wherein the first and second lines are each disposed substantially in a mid portion of the outer circumferential surface of the cannula between the upper portion and the respective right or left side portion of the outer circumferential surface.

4. The medical device of claim 2, wherein the upper portion is configured to be disposed at about the twelve o'clock position when viewed along the longitudinal axis, the right side portion is configured to be disposed at about the three o'clock position, the left side portion is configured to be disposed at about the nine o'clock position, the first visual line is configured to be disposed at about the two o'clock position, and the second visual line is configured to be disposed at about the ten o'clock position.

5. The medical device of claim 2, wherein the plurality of needles are configured to extend from the distal end portion of the cannula multiple times while the device is inserted into the patient, with the needles initially extended when first and second visual lines are equally offset from a vertical plane through the longitudinal axis, to a second extension when the device is rotated such that one of the first or second lines is oriented to substantially lie within the vertical plane.

6. The medical device of claim 5, wherein the needles are further configured to extend from the distal end portion of the cannula when the device is rotated such that the other of the first or second lines is oriented to substantially lie within the vertical plane.

7. The medical device of claim 1, wherein the device is configured to be inserted into the patient's urethra with the upper portion of the cannula facing upwardly when the patient is oriented in a lithotomy position.

8. The medical device of claim 1, wherein the second handle includes a port to selectively receive fluid therethrough and provide fluid communication with lumens disposed in each of the plurality of needles.

9. The medical device of claim 1, further comprising an imaging band disposed around the outer circumferential surface of the cannula upon the distal end portion of the cannula proximate to the plurality of apertures, wherein the imaging band is positioned such that that a tip upon the distal portion of each of the plurality of needles are positioned upon the same longitudinal position upon the cannula as the imaging band.

10. The medical device of claim 1, further comprising a plurality of depth markings disposed upon the cannula to provide an indication of the depth of insertion of the cannula within the patient.

11. The medical device of claim 1, further comprising a lock that selectively engages the first and second handles to maintain the plurality of needles in the first position.

12. The medical device of claim 11, wherein the first and second handles each include an handle aperture, with the apertures disposed in linear alignment when the plurality of needles are in the first position to accept a locking member through both handle apertures.

13. The medical device of claim 1, wherein the cannula is substantially straight and the device is configured to be inserted into the female urethra.

14. The medical device of claim 1, wherein the plurality of needles are configured to extend linearly about 7 mm from their respective aperture, and each needle is configured to exit their respective aperture at about a 40 degree angle with respect to a longitudinal axis of the cannula.

15. A medical device for treating female stress urinary incontinence, comprising:
   an elongate cannula comprising a distal end portion, a proximal end portion, and a lumen defined therethrough, an outer circumferential surface defining an upper portion, a right side portion, a bottom portion, and a left side portion each substantially equally spaced from their respective neighboring portion around the circumferential surface of the cannula, the cannula further comprising a plurality of apertures disposed through the distal end portion to provide communication from the lumen, a first of the plurality of apertures disposed on the right side portion, a second of the plurality of apertures disposed on the bottom portion, and a third of the plurality of apertures disposed on the left side portion, wherein there are no apertures disposed upon the upper portion;

a plurality of injection needles disposed within the lumen, each comprising a distal portion disposed in alignment with one of the first, second, and third apertures and a proximal end portion;

a first handle fixed with respect to the cannula and a second handle disposed in conjunction with the first handle and fixed to the proximal end portion of each of the plurality of needles, the first handle translatable with respect to the second handle to translate the plurality of needles from a first position where the distal portions of each of the plurality of needles are disposed within the lumen of the cannula, and a second position where the distal portion of each of the plurality of needles extends out of the lumen through their respective aperture; and a line applied to the outer surface of the cannula parallel to a longitudinal axis thereof and such that a central axis of the line parallel to the longitudinal axis is disposed between the upper portion and one of the right or left side portions of the outer circumferential surface of the cannula to allow the cannula to be positioned at an appropriate rotational position within the patient.

* * * * *

UNITED STATES PATENT AND TRADEMARK OFFICE
CERTIFICATE OF CORRECTION

| | | |
|---|---|---|
| PATENT NO. | : 8,298,187 B2 | Page 1 of 1 |
| APPLICATION NO. | : 12/498867 | |
| DATED | : October 30, 2012 | |
| INVENTOR(S) | : Bryan Woodard et al. | |

It is certified that error appears in the above-identified patent and that said Letters Patent is hereby corrected as shown below:

<u>In the Claims</u>

In column 12, claim 13, line 51, after "inserted into" replace "the female" with --a female--.

Signed and Sealed this
Nineteenth Day of March, 2013

Teresa Stanek Rea
*Acting Director of the United States Patent and Trademark Office*